(12) United States Patent
Ferrera et al.

(10) Patent No.: US 9,808,359 B2
(45) Date of Patent: Nov. 7, 2017

(54) TREATMENT SYSTEMS PROCESSES AND DEVICES ADDRESSING CEREBRAL VASOSPASM/VASOCONSTRICTION

(71) Applicants: David A. Ferrera, Coto De Caza, CA (US); Joshua Benjamin, Mission Viejo, CA (US); Pervinder Bhogal, London (GB); Michael Söderman, Stockholm (SE)

(72) Inventors: David A. Ferrera, Coto De Caza, CA (US); Joshua Benjamin, Mission Viejo, CA (US); Pervinder Bhogal, London (GB); Michael Söderman, Stockholm (SE)

(73) Assignee: NEURVANA MEDICAL, LLC, Tustin, CA (US)

( * ) Notice: Subject to any disclaimer, the term of this patent is extended or adjusted under 35 U.S.C. 154(b) by 0 days.

(21) Appl. No.: 15/154,927

(22) Filed: May 13, 2016

(65) Prior Publication Data
US 2017/0086992 A1    Mar. 30, 2017

Related U.S. Application Data

(60) Provisional application No. 62/253,025, filed on Nov. 9, 2015, provisional application No. 62/235,543, filed
(Continued)

(51) Int. Cl.
*A61F 2/844* (2013.01)
*A61F 2/90* (2013.01)
(Continued)

(52) U.S. Cl.
CPC .............. *A61F 2/844* (2013.01); *A61F 2/90* (2013.01); *A61F 2/966* (2013.01); *A61L 31/022* (2013.01);
(Continued)

(58) Field of Classification Search
CPC .. A61F 2/82; A61F 2/844; A61F 2/966; A61F 2/95; A61F 2/962; A61F 2002/823;
(Continued)

(56) References Cited

U.S. PATENT DOCUMENTS 8,066,757 B2 * 11/2011 Ferrera ............... A61B 17/221
                                                           606/159
8,070,791 B2    12/2011 Ferrera et al.
(Continued)

OTHER PUBLICATIONS

International Search Report for PCT/US2016/032563 dated Septemper 1, 2016 (5 pages).
(Continued)

*Primary Examiner* — Dianne Dornbusch
(74) *Attorney, Agent, or Firm* — Patastr, APC; Peter Jon Gluck

(57) ABSTRACT

Endovascular treatment of, for example, delayed cerebral vasospasm involves the placing of a microcatheter in the affected vessels followed by the teachings of the instant disclosure, which is clinically improved with comparison to slow infusion of a vasodilating compound. Systems, processes and self-expanding designed stents and stent-like members are featured and highlighted. The stents and stent-like members being retrieved, nothing is left in the vessel. Drug-eluting stents, resorbable stents and angiographically imagable coatings, including tantalum brushes over part or all of subject system components are also disclosed.

7 Claims, 6 Drawing Sheets

Related U.S. Application Data on Sep. 30, 2015, provisional application No. 62/235,361, filed on Sep. 30, 2015.

(51) Int. Cl.

| | |
|---|---|
| *A61F 2/966* | (2013.01) |
| *A61L 31/02* | (2006.01) |
| *A61L 31/14* | (2006.01) |
| *A61L 31/16* | (2006.01) |
| *A61L 31/18* | (2006.01) |
| *A61F 2/95* | (2013.01) |

(52) U.S. Cl.
CPC .............. *A61L 31/148* (2013.01); *A61L 31/16* (2013.01); *A61L 31/18* (2013.01); *A61F 2002/9528* (2013.01); *A61F 2210/0004* (2013.01); *A61F 2250/0059* (2013.01); *A61F 2250/0067* (2013.01); *A61F 2250/0098* (2013.01); *A61L 2300/416* (2013.01); *A61L 2300/418* (2013.01)

(58) Field of Classification Search
CPC ...... A61F 2002/9505; A61F 2002/9511; A61F 2002/9528; A61F 2002/9534
See application file for complete search history.

(56) References Cited

U.S. PATENT DOCUMENTS

| | | | | |
|---|---|---|---|---|
| 8,088,140 | B2 * | 1/2012 | Ferrera ................ | A61B 17/221 606/113 |
| 8,197,493 | B2 | 6/2012 | Ferrera et al. | |
| 8,545,415 | B2 * | 10/2013 | West ...................... | A61B 5/083 600/532 |
| 8,574,262 | B2 | 11/2013 | Ferrera et al. | |
| 8,585,713 | B2 * | 11/2013 | Ferrera ................... | A61F 2/01 606/127 |
| 8,926,680 | B2 * | 1/2015 | Ferrera ............ | A61B 17/12022 623/1.11 |
| 8,945,143 | B2 | 3/2015 | Ferrera et al. | |
| 8,945,712 | B2 | 3/2015 | Dams et al. | |

OTHER PUBLICATIONS

Cagatay, Andic, et al., Efficacy of endovascular treatment and feasibility of stent-assisted coiling in the presence of severe and symptomatic vasospasm; J NeuroIntervent Surg 2016;0:1-7; doi: 10.1136/neurintsurg-2016-012734.

Bhogal, paul, et al., Treatment of cerebral vasospasm with self-expandable retrievable stents: proof of concept; J NeuroIntervent Surg 2016;0:1-8. doi: 10.1136/neurintsurg-2016-012546.

Menon, Bijoy K., et al. Initial Experience with a Self-Expanding Retrievable Stent for Recanalization of Large Vessel Occlusions in Acute Ischemic Stroke, Neuroradiology (2012) 54:147-154 DOI 10.1007/s00234-010-0835-x.

Sayama, Christina M., B.S., et al. Update on Endovascular Therapies for Cerebral Vasospasm Induced by Aneurysmal Subarachnoid Hemorrhage; Neurosurg. Focus, 21 (3):E12, 2006.

Logallo, Nicola, et al. Continuous Local Intra-Arterial Nimodipine for the Treatment of Cerebral Vasospasm, Journal of Neurological Surgery Reports, vol. 76, No. R1/2015.

Bauer, Andrew M., et al. Treatment of Intracranial Vasospasm Following Subarachnoid Hemorrhage, Frontiers in Neurology, Published: May 20, 2014, Article 72, doi: 10.3389/fneur.2014.0072.

Chou, Ming-Ting, et al., Coronary Stenting for Coronary Vasospasm Complicated with Refractory Ventricular Tachycardia and Fibrillation. Acta Cardiol Sin 2012;28:145-147.

Bhogal, P, Loh, Y. Brouwer, Patrick, Andersson, Tommy, Söderman, et al. Stentplasty—Potential Mechanism of Action. 7 pages.

Pederzani, G, Watton, Paul, et al. A Mathematical Model of Cerebral Vasospasm. The University of Sheffield, INSIGNEO, Institute for in silico Medicine, SofTMech. 12 pages.

Menghini W, Brown RD, Sicks JD, et al. Incidence and prevalence of intracranial aneurysms and hemorrhage in Olmsted County, Minnesota, 1965 to 1995. Neurology 1998;51:405-11.

International Search Report for PCT/US2014/070908 dated Apr. 3, 2015 (4 pages).

International Search Report for PCT/US2015/014738 dated May 7, 2015 (2 pages).

International Search Report for PCT/US2014/033881 dated Aug. 27, 2014 (4 pages).

Kassell NF, Torner JC. Aneurysmal rebleeding: a preliminary report from the Cooperative Aneurysm Study. Neurosurgery 1983;13:479-81.

Velthuis BK. Rinkel GJ, Ramos LM, et al. Subarachnoid hemorrhage: aneurysm detection and preoperative evaulation with CT angiography. Radiology 1998:208:423-30. doi:10.1148/radiology.208.2.9680571.

Kassell NF, Torner JC, Haley EC, et al. The International Cooperative Study on the Timing of Aneurysm Surgery, Part 1: Overall management results. J Neurosurg 1990;73:18-36. doi:10.3171/jns.1990.73.1.0018.

Hijdra A, van Gijn J, Nagelkerke NJ, et al. Prediction of delayed cerebral ischemia, rebleeding, and outcome after aneurysmal subarachnoid hemorrhage. Stroke J Cereb Circ 1988;19:1250-6.

Hijdra A, Vermeulen M, van Gijn J. et al. Rerupture of intracranial aneurysms: a clinicoanatomic study. J Neurosurg 1987;67:29-33. doi: 10.3171/jns. 1987.67.1.0029.

Molyneux A, Kerr R, Stratton I, et al. International Subarachnoid Aneurysm Trial (ISAT) of neurosurgical clipping versus endovascular coiling in 2143 patients with ruptured intracranial aneurysms: a randomised trial. Lancet 2002;360:1267-74.

Kassell NF, Sasaki T. Colohan AR, et al. Cerebral vasospasm following aneurysmal subarachnoid hemorrhage. Stroke J Cereb Circ 1985;16:562-72.

Oyama K, Criddle L. Vasospasm after aneurysmal subarachnoid hemorrhage, Crit Care Nurse 2004;24:58-60, 62, 64-7.

Harrod, CG, Bendok BR. Batjer HH. Prediction of cerebral vasospasm in patients presenting with aneurysmal subarachnoid hemorrhage: a review, Neurosurgery 2005:56:633-54; discussion 633-54.

Burch CM, Wozniak MA, Sloan MA, et al. Detection of intracranial internal carotid artery and middle cerebral artery vasospasm following subarachnoid hemorrhage. J Neuroimaging off J Am Soc Neuroimaging 1996;6:8-15.

Allen GS, Ahn HS, Preziosi TJ, et al. Cerebral arterial spasm—a controlled trial of nimodipine in patients with subarachnoid hemorrhage. N Engl J Med 1983;308:619-24. doi:10.1056/NEJM198303173081103.

Pickard JD, Murray GD Illingworth R, et al. Effect of oral nimodiine on cerebral infarction and outcome after subarachnoid hemorrhage: British aneurysm nimodipine trial. BMJ 1989; 298:636-42.

Biondi A, Ricciardi GK, Puybasset L, et al. Intra-arterial nimodipine for the treatment of symptomatic cerebral vasospasm after aneurysmal subarachnoid hemorrhage: preliminary results, AJNR Am J Neuroradiol 2004;25: 1067-76.

Kim S-S, Park D-H, Lim D-J, et al. Angiographic features and clinical outcomes of intra-arterial nimodipine injection in patients with subarachnoid hemorrhage-induced vasospasm, J. Korean Neurosurg Soc 2012;52:172-8. doi:10.3340/jkns.2012.52.3.172.

Badjatia N, Topcuoglu MA, Pryor JC, et al. Preliminary experience with intra-arterial nicardipine as a treatment for cerebral vasospasm. AJNR Am J Neuroradiol 2004;25:819-26.

Hänggi D, Turowski B, Beseoglu K, et al. Intra-arterial nimodipine for severe cerebral vasospasm after aneurysmal subarachnoid hemorrhage: influence on clinical course and cerebral perfusion. AJNR Am J Neuroradiol 2008:29:1053-60. doi:10.3174/ajnr.A1005.

Lifante I, Delgado-Mederos R, Andreone V, et al. Angiographic and hemodynamic effect of high concentration of intra-arterial nicardipine in cerebral vasospasm. Neurosurgery 2008;63:1080-6; discussion 1086-7, doi:10.1227/01, NEU0000327698.66596.35.

(56) References Cited

OTHER PUBLICATIONS

Tejada JG, Taylor RA, Ugurel MS, et al. Safety and feasibility of intra-arterial nicardipine for the treatment of subarachnoid hemorrhage-associated vasospasm: Initial clinical experience with high-dose infusions. AJNR Am J Neuroradiol 2007;28:844-8.

Nogueira GG, Lev MH, Roccatagliata L, et al. Intra-arterial nicardipine infusion improves CT perfusion-measured cerebral blood flow in patients with subarachnoid hemorrhage-induced vasospasm. AJNR Am J Neuroradiol 2009;30:160-4. doi:10.3174/ajnr.A1275.

Beck J, Raabe A, Lanfermann H, et al. Effects of balloon angioplasty on perfusion and diffusion-weighted magnetic resonance imaging results and outcome in patients with cerebral vasospasm. J Neurosurg 2006;105:220-7. doi:10.3171/jns.2006.105.2.220.

Jestaedt L, Pham M, Bartsch AJ, et al. The impact of balloon angioplasty on the evolution of vasospasm-related infarction after aneurysmal subarachnoid hemorrhage. Neurosurgery 2008;62:610-7: doi: 10.1227/01.NEU.0000311351.32904.8B.

Muilzelaar JP, Zwienenberg M, Rudisill NA, et al. The prophylactic use of transluminal balloon angioplasty in patients with Fisher Grade 3 subarachnoid hemorrhage: a pilot study. J Neurosurg 1999;91:51-8. doi:10.3171/jns.1999.91.1.0051.

Turowski, B, du Mesnil de Rochemont R, Beck J, et al. Assessment of changes in cerebral circulation time due to vasospasm in a specific arterial territory; effect of angioplasty. Neuroradiology 2005;47:134-43. doi:10.1007/s00234-004-1281-4.

Zwienenberg-Lee M, Harman J, Rudisill N, et al. Effect of prophylactic transluminal balloon angioplasty on cerebral vasospasm and outcome in patients with Fisher Grade III subarachnoid hemorrhage: results of a phase II multicenter, randomized, clinical trial. Stroke J Cereb Circ 2008;39:1759-65. doi:10.1161/STROKEAHA.107.502666.

Bhogal, Pervinder, Loh, Yince, Brouwer, Patrict, Andersson, Tommy, Söderman et al. Treatment of cerebral vasospasm with self-expandable retrievable stents: proof of concept: J NeuroIntervent Surg 2016;0:1-8. doi:10.1136/neurintsurg-2016-012546.

Logallo, Nicola, Lundervik Bothun, Marianne, Guttormsen, Anne Berit, Holmaas, Gunhild, Kräkenes, Thomassen, Lars, Svendsen, Frode, Helland, Christian A et al. Continuous Local intra-arterial nimodipine for the treatment of cerebral vasospasm. J Neurol Surg Rep 2015;76:e75-e78. doi http://dx.doi.org/10.1055/s-0034-1543976.

Bauer, Andrew M., Rasmussen, Peter A. et al. Treatment of intracranial vasospasm following subarachnoid hemorrhage. Frontiers in Neurology May 2014, vol. 5, Article 72, 7 pages.

Kasell NF, Torner JC. Aneurysmal rebleeding: a preliminary report from the Cooperative Aneurysm Study. Neurosurgery 1983;13:479-81.

Beck J. Raabe A, Lanfermann H, et al. Effects of balloon angioplasty on perfusion and diffusion-weighted magnetic resonance imaging results and outcome in patients with cerebral vasospasm. J Neurosurg 2006;105:220-7. doi:10.3171/jns.2006.105.2.220.

Bhogal, P. et al. The Use of Steni-Retrievers in Cerebral Vasospasm: Karolinska University Hospital, Stockholm; Swedith Neurosciences Centre, Seattle; St. Bartholomew's & the Royal London Hospital, London.

\* cited by examiner

TREATMENT SYSTEMS PROCESSES AND DEVICES ADDRESSING CEREBRAL VASOSPASM/VASOCONSTRICTION

CROSS REFERENCE TO RELATED CASES

This case claims priority of U.S. Provisional Ser. Nos. 62/253,025; filed Nov. 19, 2015, 62/235,543; filed Sep. 30, 2015; and 62/235,361; filed Sep. 30, 2015, each of which is assigned to the instant assignee.

BACKGROUND OF THE DISCLOSURES

The present disclosures related to therapy and systems for treating the neurovascular system, in particular the present inventions relate to endovascular devices for neurovascular invention designed to impact, extenuate, mitigate or prevent vasospasm/vasoconstriction.

EXPRESSLY INCORPORATED BY REFERENCE

The following United States Letters Patents, PCT applications and all other attached publications are expressly incorporated by reference, as if fully set forth herein, to better define the state of neurovascular patent art, without any admission or preclusive status vis-à-vis the instant disclosures, rather-being invented by the instant assignee, they document the evolution of the devices and procedures comprising the Field as further developed below, disclosed, claimed and shown in the Appendices of the various documents incorporated by reference:
 PCT/US2014107090; PCT/US2015/014738; PCT/US2014/033881; and PCT/US2014/033881;
 U.S. Pat. Nos. 8,945,712; 8,926,680; 8,585,713; 8,945,143; 8,574,262; 8,545,415; 8,066,757; 8,070,791; 8,197,493; and 8,088,140.

The present inventions relate to systems for treating issues in the brain and related vasculature from injury, insult or trauma—often related or secondary to stroke, including acute conditions related to intracranial bleeding and related insults and injury, both from rupture of aneurysms and attempts to treat them.

This includes both (PCHV) Post-hemorrhagic cerebral aneurysm, DCV (see below) and those related conditions from ischemic and hemorrhagic stroke wherein vase-constriction is a modifiable risk factor.

Intracranial aneurysms which rupture, and/or those which are treated with traditional endovascular coiling or neurosurgical clipping methodologies often result in the most feared sequelae of subarachnoid hemorrhage, namely Delayed Cerebral Vasospasm (DCV).

Since DCV constitutes the leading cause of morbidity in patients admitted to tertiary care hospitals, it would be expected that advances in the devices and approaches which have occurred, for example, in endovascular coiling and related techniques would have been used to address this ongoing clinical need. Unfortunately, prior to the advent of the instant teachings this has not been the case to the extent that practitioners need it to be to achieve optimal clinical outcomes.

OBJECTIVES OF THE DISCLOSURES AND SUMMARIES

Briefly stated, in patients refractory to standard medical treatment, endovascular treatment of, for example, delayed cerebral vasospasm involves the placing of a microcatheter in the affected vessels followed by the teachings of the instant disclosure, which is believed to be clinically improved with prior existing approaches such as balloon dilatation (or dilatation with a COMANECI® brand of device by Rapid Medical of Israel or similar) and in comparison to slow infusion of a vasodilating compound. Systems, processes and self-expanding designed stents and stent-like members are featured and highlighted. The stents and stent-like members being recovered and retrieved, nothing is left in the vessel.

It is respectfully proposed that the traumatic nature of balloon dilatation, owing to the paucity of ability to control radial force, militates strongly for a solution to vasospasm, which is more atraumatic. Likewise, it is optimal to avoid arterial rupture secondary to over dilation of the vessel, dissection and related sequelae.

Similarly, it is respectfully submitted that local infusion of calcium channel blockers, such as Nimodipine causes blood pressures to drop (not good risk for vasospasm patients), is not effective in all patients and is temporary.

According to the disclosures there is shown a novel enhanced treatment system for cerebral arterial vasospasm secondary to subarachnoid hemorrhage, trauma or other conditions, which comprises, in combination, a guide catheter effective for emplacement in the ICA/VCA;
Heparin and/or related compounds in treatment-based aliquots, imaging, comprising angiograms, at least a microcatheter and microguidewire, at least a retrievable self-expanding stent, with radial forced tuned to the application, and sheath-means for covering and advancing the at least a retrievable stent to a target zone, for a predetermined time interval.

According to the disclosures there are shown procedures with the above.

EXEMPLARY ISSUE BEING ADDRESSED BY THE DISCLOSURES

Figure 1:
FIG. 1 shows an angiogram with ostensive vasospasm issues.

Delayed Cerebral Vasospasm Secondary to Acute Sub-arachnoid Haemorrhage

Background

Sub-Arachnoid Haemorrhage, Delayed Cerebral Vasospasm and Delayed Cerebral Injury
Sub-arachnoid haemorrhage (SAH) is a life threatening condition with an incidence of approximately 7-10 per 100000 patient years N. The diagnosis relies upon a high clinical index of suspicion and performing the necessary investigations that include initially a Computed Tomography (CT) scan of the head alongside CT angiography of the intracranial vessels followed by a delayed lumbar puncture if the CT scan is negative but suspicion is high.

Of all the causes of subarachnoid haemorrhage ruptured aneurysm arising from the circle of Willis accounts for approximately 85% [2-4]. Of the remaining 15% that are not attributable to saccular aneurysms, ⅔ are caused by non-aneurysmal SAH and the remaining 5% are caused by a variety of rare conditions.

The early prognosis of patients with aneurysmal SAH is most closely correlated to three variables [5,6]:
1. The neurological condition of the patient on admission.
2. The age of the patient
3. The amount of blood on the initial CT scan.

Of these variables, the initial neurological condition of the patient at admission, especially the level of consciousness, is the most important determinant [6] and the causes of an early acute deterioration in the status of the patient can be due to a variety of different factors such as hydrocephalus, early re-bleeding, or intra-cerebral haematoma.

The goal of treatment for aneurysmal subarachnoid haemorrhage is to prevent re-bleeding of the aneurysm, which has been estimated at between 35-40% in the first 4 weeks [7]. This can be done via two well-established methods—endovascular coiling of the aneurysm or neurosurgical clipping of the aneurysm. After the results of the International Subarachnoid Aneurysm Trial (ISAT) [8] endovascular coiling has gained widespread acceptance and the choice between coiling or clipping is often decided following a multi-disciplinary team meeting between the neurosurgeons and interventional neuroradiologists. The procedure is performed as soon as possible after the admission of the patient. These treatments are effective in securing the aneurysm and preventing early re-rupture of the aneurysm however, delayed consequences of the initial subarachnoid haemorrhage can have a devastating effect on the clinical outcome of patients. The most feared delayed sequelae of subarachnoid haemorrhage are Delayed Cerebral Vasospasm (DCV) and Delayed Cerebral Injury (DCI). Other terms such as Delayed Ischaemic Neurological Deficit (DIND, DID) are also used in the literature as synonyms.

Delayed cerebral vasospasm is the leading cause of morbidity and mortality in patients who have ruptured intracranial aneurysm and who are admitted to tertiary care hospitals [5,9]. Delayed cerebral vasospasm typically occurs between 3-21 days after the initial insult and may last for 12-16 days [10]. At day 7 post-ictus up to 70% of patients will demonstrate angiographic evidence of cerebral arterial vasospasm and approximately 30% of patients will go on to develop neurological deficits, termed 'symptomatic vasospasm' [11]. Angiography done during this time will often reveal diffuse vasoconstriction of the major intracranial vessels that frequently involves the terminal internal carotid artery [12] with some evidence that points towards the location of the blood being closely related to the site of vascular vasospasm and the development of delayed cerebral vasospasm and ischaemia within this territory [13].

To date the only drug of proven benefit that is routinely used in the prevention of delayed cerebral vasospasm secondary to subarachnoid haemorrhage is Nimodipine, a dihydropyridine L-Type voltage gated calcium channel antagonist. This is given orally 60 mg every 4 hours for 21 days. Allen et al. [14] were the first to publish their findings in the New England Journal of Medicine with further studies also demonstrating the protective effects of this medication [15, 16]. However, the exact mechanism as to how calcium channel antagonists prevent or relieve vasospasm is not clearly understood and the evidence about efficacy and dosage is based on a single large trial [16]. It is important to note that without the data from this single large trial the advantage of nimodipine in these patients cannot be statistically seen. Therefore, the use of nimodipine is not without question, In patients that develop cerebral vasospasm there is a risk of infarction that can be widespread. Therefore, in order to prevent infarctions from developing medical treatment is optimised to attempt to maintain perfusion. This involves increasing the blood pressure, normally between 160-200 mmHg (if the patient has had the aneurysm treated), haemodilution and hypervolaemia. Despite this some patients continue to deteriorate and in these patients endovascular treatment options are used.

In patients refractory to standard medical treatment endovascular treatment of delayed cerebral vasospasm involves the placing of a microcatheter in the affected vessels followed by the slow infusion of a vasodilating compound, normally over the course of 5-30 minutes. Numerous different agents have been used including papevarine, as well as calcium channel antagonists verapamil, nimodipine [17, 18] and nicardipine [19]. All these agents have demonstrated an affect on the cerebral vasospasm and it is believed that agents with longer half-lives may offer a more sustained and long-lasting effect [19]. It is important to note that there is no level 1 evidence to support the use of any of the aforementioned agents, although numerous smaller trials have demonstrated improvement [17,19-23] with different agents used in different institutions.

Alternatively, the spastic vessels can be dilated mechanically using balloons. There are numerous publications on this technique going back as far as 1984. Improvements in vessel diameters as well as neurological deficits were observed in most studies following balloon angioplasty and successful treatment translated into a reduced incidence of delayed cerebral ischaemia on radiographic imaging in several studies [24-28]. However, balloon angioplasty is not without risk and vessel rupture and death have been reported [29].

The exact cause for delayed cerebral vasospasm and delayed cerebral injury is not completely understood, however as outlined above the prevention or early treatment of cerebral vasospasm seems to improve patient outcome.

REFERENCES

1. Menghini V V, Brown R D, Sicks J D, et el. Incidence and prevalence of intracranial aneurysms and hemorrhage in Olmsted County, Minnesota, 1965 to 1995. *Neurology* 1998; 51:405-11.
2. Van Gijn J, van Dongen K J. Computerized tomography in subarachnoid hemorrhage: difference between patients with and without an aneurysm on angiography. *Neurology* 1980; 30:538-9.
3. Kassell N F, Torner J C. Aneurysmal rebleeding: a preliminary report from the Cooperative Aneurysm Study. *Neurosurgery* 1983; 13:479-81.
4. Velthuis B K, Rinkel G J, Ramos L M, et al. Subarachnoid hemorrhage: aneurysm detection and preoperative evaluation with CT angiography. *Radiology* 1998; 208:423-30. doi:10.1148/radiology.208.2.9680571
5. Kassell N F, Torner J C, Haley E C, et al. The International Cooperative Study on the Timing of Aneurysm Surgery.

Part 1: Overall management results. *J Neurosurg* 1990; 73:18-36. doi:10.3171/Ths.1990.73.1.0018
6. Hijdra A, van Gijn J, Nageikerke N J, et al. Prediction of delayed cerebral ischemia, rebleeding, and outcome after aneurysmal subarachnoid hemorrhage. *Stroke J Cereb Circ* 1988; 19:1250-6.
7. Hijdra A, Vermeulen M, van Gijn J, et al. Rerupture of intracranial aneurysms: a clinicoanatomic study. *J Neurosurg* 1987; 67:29-33. doi:10.3171/jns.1987.67.1.0029
8. Molyneux A, Kerr R, Stratton I, et al. International Subarachnoid Aneurysm Trial (ISAT) of neurosurgical clipping versus endovascular coiling in 2143 patients with ruptured intracranial aneurysms: a randomised trial. *Lancet* 2002; 360:1267-74.
9. Kassell N F, Sasaki T, Colohan A R, et al. Cerebral vasospasm following aneurysmal subarachnoid hemorrhage. *Stroke J Cereb Circ* 1985; 16:562-72.
10. Oyama K, Criddle L. Vasospasm after aneurysmal subarachnoid hemorrhage. *Crit Care Nurse* 2004; 24:58-60,62,64-7.
11. Harrod C G, Bendok B R, Batjer H H. Prediction of cerebral vasospasm in patients presenting with aneurysmal subarachnoid hemorrhage: a review. *Neurosurgery* 2005; 56:633-54; discussion 633-54.
12. Burch C M, Wozniak M A, Sloan M A, at al. Detection of intracranial internal carotid artery and middle cerebral artery vasospasm following subarachnoid hemorrhage. *J Neuroimaging Off J Am Soc Neuroimaging* 1996; 6:8-15.
13. Kistler J P, Crowell R M, Davis K R, at al. The relation of cerebral vasospasm to the extent and location of subarachnoid blood visualized by CT scan: a prospective study. *Neurology* 1983; 33:424-36.
14. Allen G S, Ahn H S, Preziosi T J, et al. Cerebral arterial spasm—a controlled trial of nimodipine in patients with subarachnoid hemorrhage. *N Engl J Med* 1983; 308:619-24. doi:10.1056/NEJM198303173081103
15. Philippon J, Grob R, Dagreou F, et al. Prevention of vasospasm in subarachnoid hemorrhage. A controlled study with nimodipine. *Acta Neurochir (Wien)* 1986; 82:110-4.
16. Pickard J D, Murray G D, Illingworth R, at al. Effect of oral nimodipine on cerebral infarction and outcome after subarachnoid hemorrhage: British aneurysm nimodipine trial. *BMJ* 1989; 298:636-42.
17. Biondi A, Ricciardi G K, Puybasset L, at al. Intra-arterial nimodipine for the treatment of symptomatic cerebral vasospasm after aneurysmal subarachnoid hemorrhage: preliminary results. *AJNR Am J Neuroradiol* 2004; 25:1067-76.
18. Kim S-S, Park D-H, Um D-J, at al. Angiographic features and clinical outcomes of intra-arterial nimodipine injection in patients with subarachnoid hemorrhage-induced vasospasm. *J Korean Neurosurg Soc* 2012; 52:172-8. doi:10.3340/jkns.2012.52.3.172
19. Badjatia N, Topcuoglu M A, Pryor J C, et al. Preliminary experience with intra-arterial nicardipine as a treatment for cerebral vasospasm. *AJAR Am J Neuroradiol* 2004; 25:819-26.
20. Hänggi D, Turowski B, Beseoglu K, et al. Intra-arterial nimodipine for severe cerebral vasospasm after aneurysmal subarachnoid hemorrhage: influence on clinical course and cerebral perfusion. *AJNR Am J Neuroradiol* 2008; 29:1053-60. doi:10.3174/ajnr.A1005
21. Linfante I, Delgado-Mederos R, Andreone V, et al. Angiographic and hemodynamic effect of high concentration of intra-arterial nicardipine in cerebral vasospasm. *Neurosurgery* 2008; 63:1080-6; discussion 1086-7. doi: 10.1227/01.NEU.0000327698.66596.35
22. Tejada J G, Taylor R A, Ugurel M S, at al. Safety and feasibility of intra-arterial nicardipine for the treatment of subarachnoid hemorrhage-associated vasospasm: initial clinical experience with high-dose infusions. *AJNR Am J Neuroradiol* 2007; 28:844-8.
23. Nogueira R G, Lev M H, Roccatagliata L, at al. Intra-arterial nicardipine infusion improves CT perfusion-measured cerebral blood flow in patients with subarachnoid hemorrhage-induced vasospasm. *AJNR Am J Neuroradiol* 2009; 30:160-4. doi:10.3174/ajnr.A1275
24. Beck J, Raabe A, Lanfermann H, at al. Effects of balloon angioplasty on perfusion- and diffusion-weighted magnetic resonance imaging results and outcome in patients with cerebral vasospasm. *J Neurosurg* 2006; 105:220-7. doi:10.3171/jns.2006.105.2.220
25. Jestaedt L, Pham M, Bartsch A J, et al. The impact of balloon angioplasty on the evolution of vasospasm-related infarction after aneurysmal subarachnoid hemorrhage. *Neurosurgery* 2008; 62:610-7; discussion 610-7. doi:10.1227/01.NEU.0000311351.32904.8B
26. Muizelaar J P, Zwienenberg M, Mini N A, et al. Safety and efficacy of transluminal balloon angioplasty in the prevention of vasospasm in patients with Fisher Grade 3 subarachnoid hemorrhage: a pilot study. *Neurosurg Focus* 1998; 5:e5.
27. Muizelaar J P, Zwienenberg M, Rudisill N A, et al. The prophylactic use of transluminal balloon angioplasty in patients with Fisher Grade 3 subarachnoid hemorrhage: a pilot study. *J Neurosurg* 1999; 91:51-8. doi:10.3171/jns.1999.91.1.0051
28. Turowski B, du Mesnil de Rochemont R, Beck J, at al. Assessment of changes in cerebral circulation time due to vasospasm in a specific arterial territory: effect of angioplasty. *Neuroradiology* 2005; 47:134-43. doi:10.1007/s00234-004-1281-4
29. Zwienenberg-Lee M, Hartman J, Rudisill N, at al. Effect of prophylactic transluminal balloon angioplasty on cerebral vasospasm and outcome in patients with Fisher grade III subarachnoid hemorrhage: results of a phase II multicenter, randomized, clinical trial. *Stroke J Cereb Circ* 2008; 39:1759-65. doi:10.1161/STROKEAHA.107.502666.

DETAILED DESCRIPTION OF THE DISCLOSURE

The present inventors have discovered effective ways to impact vasospasm, and improved devices to do so and create better clinical outcomes.

As briefly summarized above, despite rapid advancement in the minimally invasive and neurovascular fields, there does not seem to be a synergistic leveraging of techniques and devices to make outcomes best for patients—given the number of tools.

Lessons learned from open and closed cell stenting in the brain, for example U.S. Letters Patent numbers [to be filled in '140] U.S. Pat. No. 8,197,493 each expressly incorporated by reference above, need to be used to overcome those issues, which balloon dilatation and pharmacology cannot address adequately in terms of vasospasm.

Turning to FIG. 1, an angiogram shows that within the target brain area vessels are subject to vasospasm as known to those skilled in the art.

Figure 2:
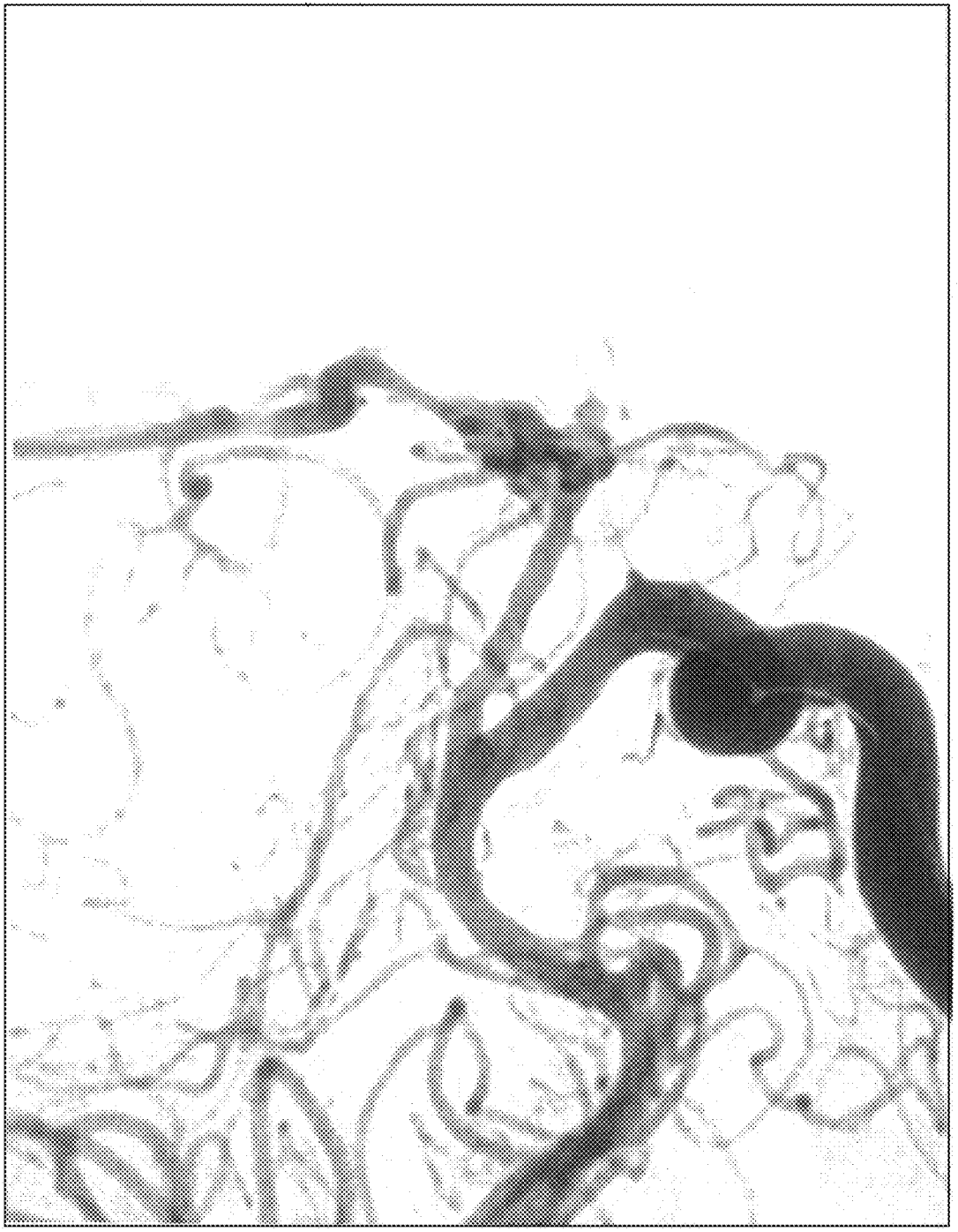
FIG. 2 shows a completion angiogram according to the instant teachings.
Figures 3, 4:
FIG. 3 similarly shows a severely impacted vessel including vasospasm.
FIG. 4 shows the follow-up shot wherein the vessel is stabilized by aspects of teachings of the present invention, namely deployment of the objects of the present invention.
Figure 6:
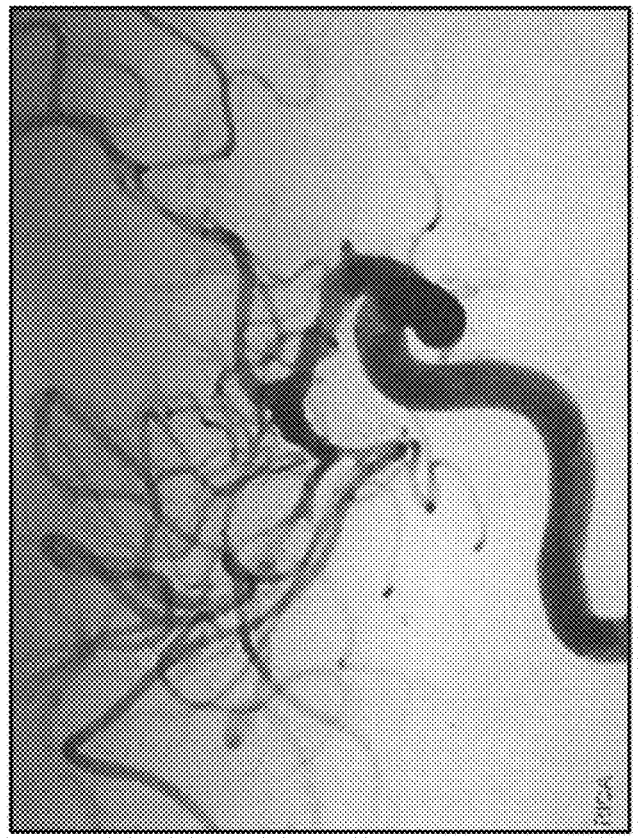
FIG. 6 also between the arrows shows how the system of the present invention leads the vessels from a first vasospasmed state to a second patent state.
Figure 5:
FIG. 5 shows that a vessel in spasm, even with nimodipine, can clearly seen to be blocked.

FIG. 2 shows the follow-up shot wherein the vessel is stabilized by aspects of teachings of the present invention;

FIG. 3 similarly shows a severely impacted vessel including vasospasm;

FIG. 4 shows the follow-up shot wherein the vessel is stabilized by aspects of teachings of the present invention, namely deployment of the objects of the present invention;

FIG. 5 shows that a spasmed vessel, even with nimodipine, can clearly seen to be blocked;

FIG. 6 also between the arrows shows how the system of the present invention leads the vessels from a first vasospasmed state to a second patent state.

Figure 7:
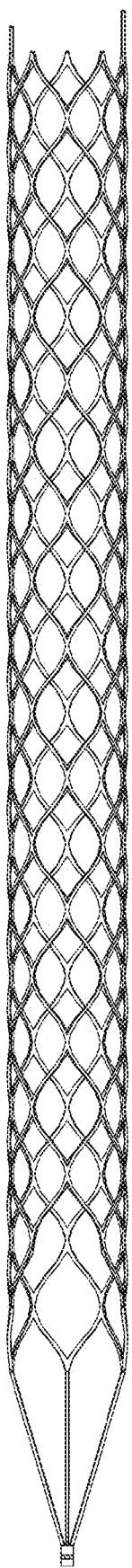
FIG. 7 shows an exemplary stenting-means, have a multiplicity of smaller cells which works in conjunction with an elongated system.
Figure 8:
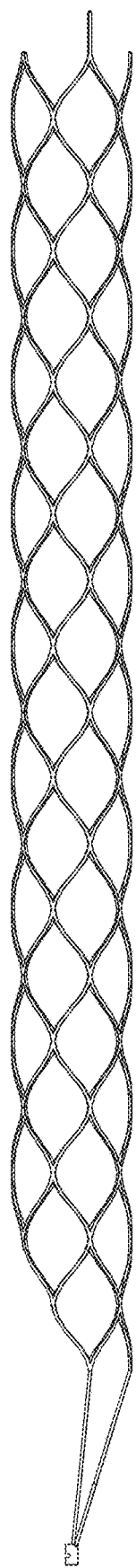
FIG. 8 likewise shows an exemplary stenting-means, have a multiplicity of smaller cells which works in conjunction with an elongated system.

FIG. 7 and FIG. 8 demonstrate what has been discovered, unexpectedly mitigating or preventing vasospasm, namely longer stents with many smaller cells and radial force which can be tuned for this application. Referring now to FIG. 7, as discussed the nature of the stent/device/stenting-means has a specifically designed cell structure which includes many cells generally of an open variety, whereby an extended length (eg. At least about 50 cm) allows for trackability and flexibility, balanced with a proper amount of control for deployment.

Referring now also to FIG. 8, self-expanding nitinol stenting-means is shown with small cells which deliver optimum control and radial force for the treatment of disease. Artisans understand that having access with longer stents having smaller cells and radial force tuned to the neurovascular need undergirds much of the instant solution. Since this problem was discovered and overcome by the instant teachings, others may now continue to advance the science of prevention of vasospasm.

Exemplary Indication

The instant teachings uniquely add tools to the practitioner's arsenal for treating—for example, a cerebral arterial vasospasm secondary to subarachnoid hemorrhage, trauma or other condition. Artisans understand that this method applies to related methods of treatment.

The Procedure for those skilled in the art includes, for example the following steps. Artisans understand swapping steps and substitutions and additions are all within the scope of the list below, which comprises merely guidance as to one approach for performing according to the present invention:

A guiding catheter should be placed in the Internal Carotid Artery or Vertebral Artery.

Heparinization to double ACT-level.

A diagnostic angiogram is performed in order to visualize the location and extent of the arterial spasm and exclude other pathologies that may be contraindications to the treatment.

The MCA, ACerA or PCerA is catherized to the M2, A2 or P2 segment with a microcatheter (MC) and microguidewire. In case this is not necessary or cannot be safely done the tip of the MC may be placed in the M1, A1 or P1.

The microguidewire is removed.

The temporary stent is inserted in the MC and advanced to the tip of the MC.

The temporary stent is kept in place while the MC is withdrawn to the level of the proximal end of the stent. The stent is thus deployed without being advanced or retracted.

Control angiography through the guiding catheter.

The temporary stent is kept in place for 3-10 minutes.

Resheating of the temporary stent by advancing the MC while the stent is kept immobile.

Retraction of the MC to the ICA or Vert Art with the stent still inside.

Control angiography through the guiding catheter.

The procedure may be repeated in the same or other vessels.

Nimodipine (Ca+-channel blockers) can be given in the MC during the stent deployment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2, Intel Core Duo, AMD Phenom II X4, Intel Core i5 Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A treatment methodology for vasospasm secondary to another procedure, which comprises the steps listed in the order presented:
   Emplacing a guide catheter system into a neurological image confirmed vasospasmed vessel;
   Following said guide catheter with a self-expanding sheathed retrievable specialized stent, having radial force sufficient to dilatate the subject vessel;
   Wherein the specialized stent comprising self-expanding modular units having a multiplicity of smaller cells, being open or closed celled and elongated longitudinally from distal to proximal ends;
   Whereby the specialized stent is kept in place while a microcatheter (MC) is withdrawn to the level of a proximal end of the specialized stent, the specialized stent is thus deployed without being advanced or retracted;
   The specialized stent is kept in place for at least about less than five minutes;
   Resheathing of the specialized stent by advancing the MC while the specialized stent is kept immobile; and
   Retraction of the MC to the Internal Carotid Artery (ICA) or Vertebral Artery (Vert Art) with the specialized stent still inside; then Control angiography through the guiding catheter to confirm vessel status and optionally
   Said procedure may be repeated in the same or other vessels to achieve long term dilatation of the vessel without vasospasm.

2. The improved treatment claim 1, herein, the specialized stent further comprising at last one device from the group consisting essentially of a drug eluting stent; a bioresorbable stent (bioresorbable stents/scaffold made either from magnesium based material) and/or Polylactic acid based polymers; a bare-metal self-expanding stent and chimeric combinations or hybrids of the same, whereby the procedure time lowers the potential for vessel rupture.

3. The improved treatment methodology of claim 2, further comprising:
   a coating, marker, system for marking or covering which is radiopaque wherein the coating, marker, system for marking or covering is disposed partially over a portion only of the surface of any device associated herewith and the ability to inject Heparin and/or vasodilators during stent deployment; providing long lasting cerebral vasodilation for patients with delayed vasospasm.

4. A method of treatment of cerebral vasospasm secondary to another procedure with a non-detachable specialized stent which comprises the steps listed in the order presented:

Emplacement of a guiding catheter within the Internal Carotid Artery (ICA) or Vertebral Artery (Vert Art) of a patient;

Heparinization of the patient to double Activated Clot Time (ACT)-level;

Performing a diagnostic angiogram in order to visualize the location and extent of the arterial spasm and exclude other pathologies that may be contraindications to the treatment;

Catheterizing the Middle cerebral artery (MCA), Anterior Cerebral Artery (ACerA) or (PCerA) at least to the M2, A2 or P2 segment with a microcatheter (MC) and microguidewire;

wherein in cases where this is not necessary or cannot be safely done the tip of the MC may be placed in the MI, A1 or PI;

Removal of the microguidewire;

Inserting the non-detachable specialized stent in the MC and advancement of the same to the tip of the MC;

Wherein the non-detachable specialized stent comprising self-expanding modular units having a multiplicity of smaller cells, being open or closed celled and elongated longitudinally from distal to proximal ends;

Whereby the non-detachable specialized stent is kept in place while the MC is withdrawn to the level of the proximal end of the non-detachable specialized stent, the non-detachable specialized stent is thus deployed without being advanced or retracted;

Control angiography through the guiding catheter;

The non-detachable specialized stent is kept in place for at least about 5 minutes;

Resheathing of the non-detachable specialized stent by advancing the MC while the non-detachable specialized stent is kept immobile; and Retraction of the MC to the Internal Carotid Artery (ICA) or Vert Art with the non-detachable specialized stent still inside; then Control angiography through the guiding catheter, optionally, Said procedure may be repeated.

5. The method of treatment of claim 4, whereby said stent is self-expanding, and whereby Calcium (Ca+)-channel blockers are given in the MC during the stent deployment.

6. The stent defined in claim 5, wherein said medical device is removable, said device being retrieved, nothing is left in the vessel, yet long term vasodilation is achieved.

7. The stent defined in claim 6, wherein said medical device is atraumatic, low profile, radiopaque, and has a robust geometry along with being removable, said devices further comprising at least a drug covering or coating selected from the group of Everolimus; Paclitaxel; Sirolimus; Corolimus and any related compounds, salts, moieties which potentially reduce risk of thrombosis, lumen loss and related challenges and/or the stent/stent-means is bioresorbable stents/scaffold made either from magnesium based material and/or Polylactic Acid-based (PLA's) (polymer), that could be implanted for vasospasm as a treatment, which specifically designed high-radial force devices.

* * * * *

UNITED STATES PATENT AND TRADEMARK OFFICE
CERTIFICATE OF CORRECTION

PATENT NO. : 9,808,359 B2
APPLICATION NO. : 15/154927
DATED : November 7, 2017
INVENTOR(S) : David A. Ferrera et al.

It is certified that error appears in the above-identified patent and that said Letters Patent is hereby corrected as shown below:

On the Title Page

Item (74) should read:
(74) Attorney, Agent, or Firm - Patnstr, APC; Peter Jon Gluck Signed and Sealed this
Thirtieth Day of January, 2018

Joseph Matal
*Performing the Functions and Duties of the
Under Secretary of Commerce for Intellectual Property and
Director of the United States Patent and Trademark Office*